United States Patent
Rivera

(10) Patent No.: US 8,479,751 B2
(45) Date of Patent: Jul. 9, 2013

(54) PLIER-TYPE POWER FLOSSER

(76) Inventor: Edris Rivera, Oviedo, FL (US)

(*) Notice: Subject to any disclaimer, the term of this patent is extended or adjusted under 35 U.S.C. 154(b) by 482 days.

(21) Appl. No.: 12/564,895

(22) Filed: Sep. 22, 2009

(65) Prior Publication Data

US 2010/0071716 A1 Mar. 25, 2010

Related U.S. Application Data

(60) Provisional application No. 61/099,522, filed on Sep. 23, 2008.

(51) Int. Cl.
*A61C 15/00* (2006.01)

(52) U.S. Cl.
USPC ............................................. 132/327

(58) Field of Classification Search
USPC ............. 132/323, 324, 326, 327, 325; 81/427
See application file for complete search history.

(56) References Cited

U.S. PATENT DOCUMENTS

| | | | | |
|---|---|---|---|---|
| 5,816,271 A | * | 10/1998 | Urso | 132/322 |
| 5,819,769 A | * | 10/1998 | Gutierrez | 132/327 |
| 5,822,915 A | * | 10/1998 | Walker | 43/53.5 |
| 6,394,103 B1 | * | 5/2002 | Forsyth, III | 132/323 |

* cited by examiner

*Primary Examiner* — Todd Manahan
*Assistant Examiner* — Brianne Kalach

(57) ABSTRACT

A dental plier-type tool is provided for removing debris that is trapped or lodged between teeth without applying pressure to the adjacent teeth or crown itself and thus avoiding loosening the teeth (or crown). The current method for removing debris that is lodged between the teeth is usually accomplished by either of the following methods . . . manual flossing, a flossing type tool, a dental scaler, or a dental explorer. The problem with the current methods is that they all transfer unnecessary up and down, side to side pressure to the adjacent teeth or crown as pressure is being applied to the debris being dislodged, thus risking the chance of loosening the teeth (or crown). The uniqueness and advantage of the present invention is that, when used in conjunction with floss that has been properly mounted on the tool and under the debris, it transfers all it's "plier-type" power only to the debris being removed while holding the adjacent teeth or crown firmly in place. This eliminates the risk of loosening the adjacent teeth or crown.

4 Claims, 4 Drawing Sheets

PLIER-TYPE POWER FLOSSER

CROSS-REFERENCE TO RELATED APPLICATIONS

This application claims the benefit of Provisional Application 61/099,522, filed on Sep. 23, 2008.

BACKGROUND AND SUMMARY OF THE INVENTION

The device describe herein came about because I found myself in a situation where I had a particle lodged between a tooth and a crown. In trying to dislodge the particle from between my teeth, I ended up loosening my crown and had to make a trip to the dentist to have it re-glued. With the proposed device, the user can easily remove debris that is trapped or lodged between the teeth without applying pressure to the adjacent teeth or crown itself and thus avoiding loosening the teeth (or crown). The current method for removing debris that is lodged between the teeth is usually accomplished by either of the following methods . . . manual flossing, a flossing type tool, a dental scaler, or a dental explorer. The problem with the current methods is that they all transfer unnecessary up and down, side to side pressure to the adjacent teeth or crown as pressure is being applied to the debris being dislodged, thus risking the chance of loosening the teeth (or crown).

The uniqueness and advantage of the present invention is that, when used in conjunction with floss that has been properly mounted on the tool and under the debris, it transfers all it's "plier-type" power only to the debris being removed while holding the adjacent teeth or crown firmly in place. This eliminates the risk of loosening the adjacent teeth or crown.

The following patents are considered generally representative of the current state of the dental flosser art: U.S. Pat. No. 5,819,769 issued Oct. 13, 1998; U.S. Pat. No. 6,394,103 issued May 28, 2002; U.S. Pat. No. 5,004,419 issued Apr. 2, 1991; U.S. Pat. No. 6,161,556 issued Dec. 19, 2000.

DESCRIPTION OF THE INVENTION

FIG. 1 is a 3-D view which is comprised of a plier that has two slits 10a and 10b on tips 8 and 9. It also has two smaller slits 11a and 11b at the end of both handles 6 and 7. Having slits on both handles and both tips (symmetrical), allows the pliers to be used on any side in any hand. Notice that, unlike conventional pliers, when you squeeze the handles together, the tips 8 and 9 open (separate) instead of close. An optional spring 5 can be added to maintain tips 8 and 9 closed when handles are not being squeezed.

FIG. 2 is the top view. It shows all four slits completely open from top to bottom such that both slits 11a and 11b in the handles 6 and 7 are aligned with each other and both slits 10a and 10b in the tips 8 and 9 are also aligned with each other.

FIG. 3 is the side view. It shows the dental floss 14 completely installed on the invention. Notice how the floss 14 is wrapped around debris 13 which is lodged between teeth 12a and 12b. The floss is fed through slits 10a and 10b stretched over the top of the pliers and slid through slit 11a (FIG. 1). The floss is then wrapped 15 around the end of handle 6 as it's being held tight in place. This process is explained more clearly in the following figures. At this point the tool is ready to dislodge the debris. Squeezing handles 6 and 7, causes tips 8 and 9 to separate. This in turn causes tip 8 to pull the floss up through slit 10b (which stays resting on top of teeth 12a and 12b). As the floss applies an upward force directly on the debris, the slit 10b (which is part of tip 9) applies an equal and opposite (downward) force on the teeth. Applying this basic law of physics, is the key to this invention setting it apart from all other methods. As the handles of the pliers are squeezed harder, the net upward force on the debris increases, while the net force applied to the teeth or crown is zero (0). Why is this so? In this invention, for every pound of upward force applied to the teeth by the floss, a downward force of equal amount is applied on the teeth by the tip 9, resulting in a total net force of zero (0) on the teeth or crown. Since there is no force holding down the debris, the debris will eventually be dislodged without loosening the teeth or crown. In current methods available, all upward force applied to the debris is also transferred to the teeth, as long as the debris is fixed to the teeth and doesn't dislodge. Because there is no counter force (downward) to hold the teeth in place, the teeth or crown can come loose. This is better illustrated in FIGS. 10 and 11.

Figure 5:
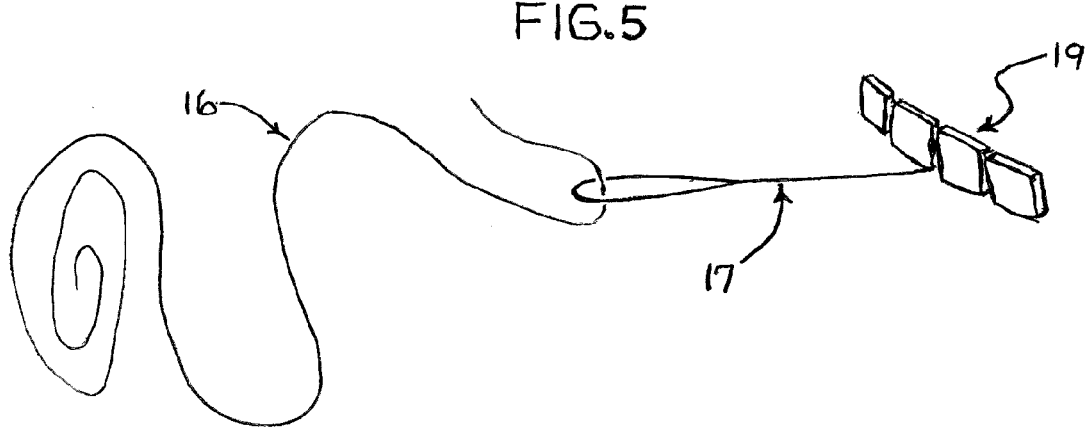
FIGS. 5 through 9 illustrate step by step the easiest way to set up the floss on the present invention.

FIG. 5 shows the floss 16 being fed through the space below the debris 19 with a standard floss feeder 17.

Figure 6:
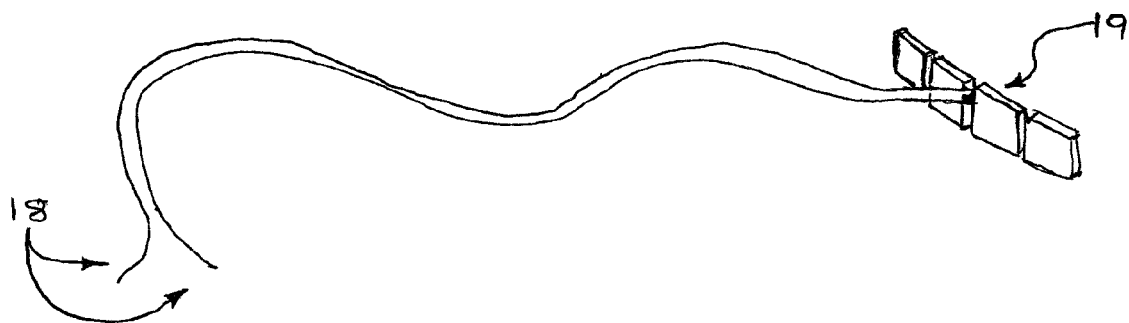

FIG. 6 shows the floss being looped around the debris 19 and both ends brought together at 18.

Figure 7:
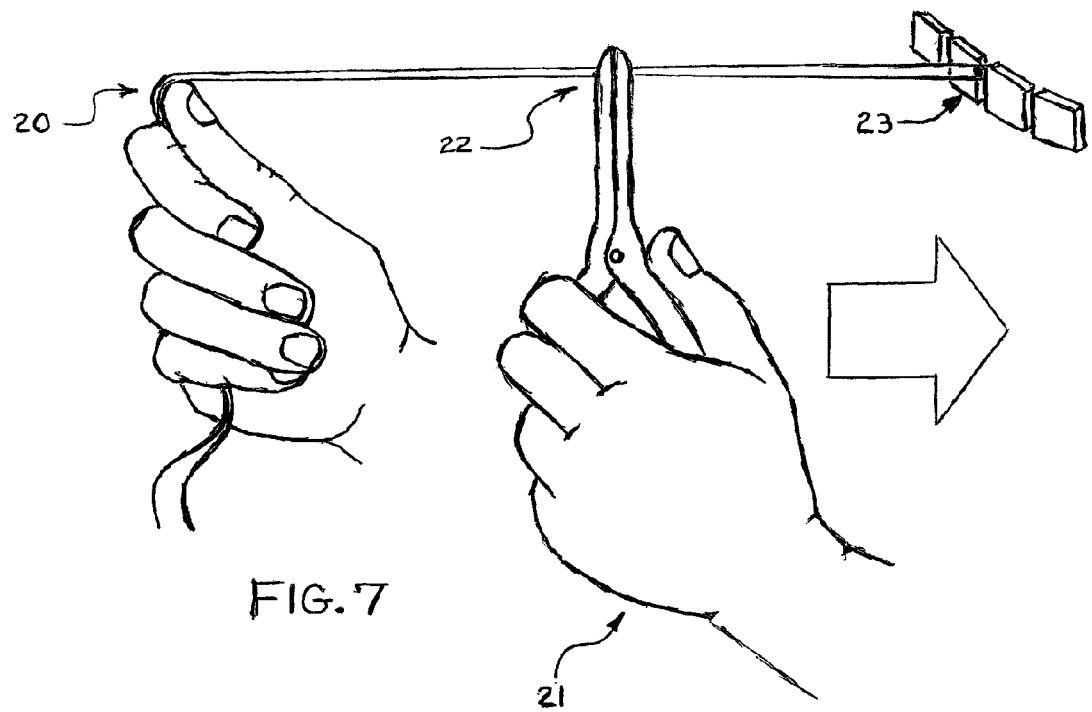

FIG. 7 shows the hand and tool placements. The floss, which has been looped around the debris 23, is being held straight by the right hand 20 while the left hand 21, while holding the pliers, engages the floss from underneath in the slits of the tips of the pliers at 22. The left hand now slides the pliers towards the teeth landing it's tip right on top of the teeth as in FIG. 8. (Note: This is the procedure used when removing a particle from the lower teeth. To remove a particle from the upper teeth, the left hand 21, while holding the pliers, would engage the floss from above the floss instead of from underneath as described in this paragraph. The left hand would then slide the pliers towards the teeth landing it's tip on the upper teeth.)

Figure 3:
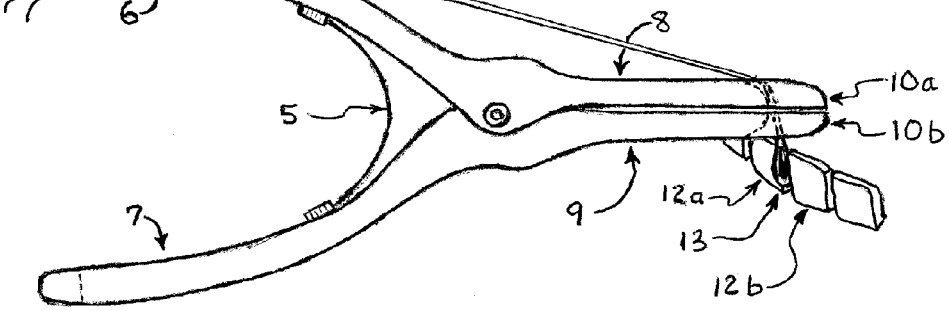
Figure 4:
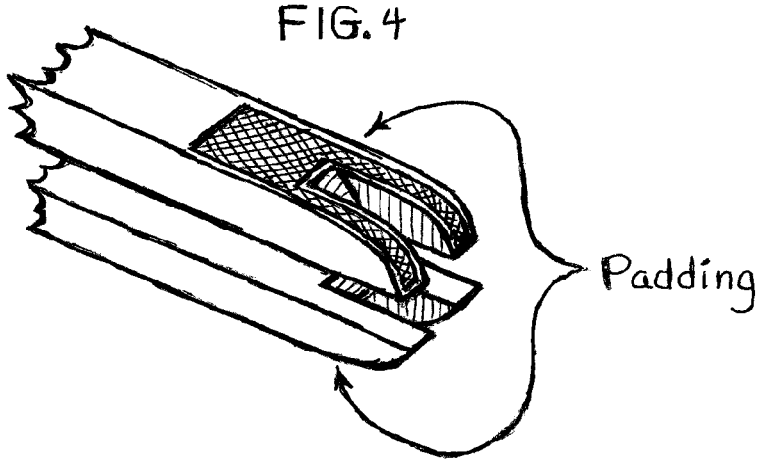
FIG. 4 illustrates an optional rubber padding that can be added to soften the recoil action which occurs the moment the debris is dislodged.
Figure 8:
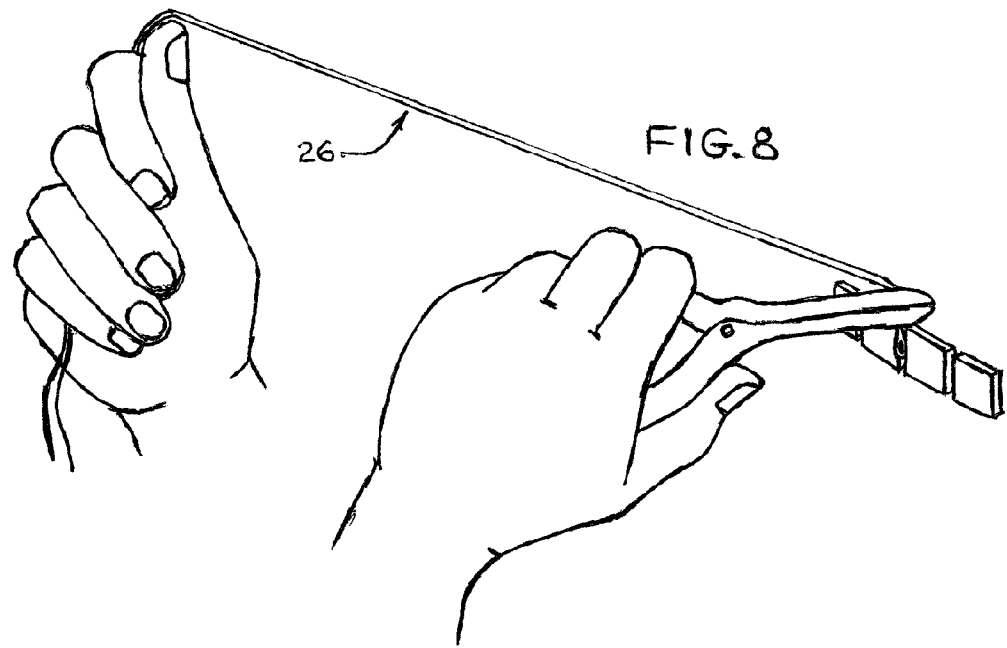

FIG. 8 shows the floss 26 slightly elevated at a slant to allow room for the pliers to be placed on the teeth. Referring back to FIG. 3, the floss 14 (which is floss 26 in FIG. 8) is stretched back towards the tip of handle 6 and fed through slit 15. While pulling the floss tightly through slit 15, it is wrapped around the tip of handle 6 in such a way that the floss 14 remains taught. The pliers is now ready to be squeezed to dislodge the debris as illustrated in FIG. 9.

Figure 9:
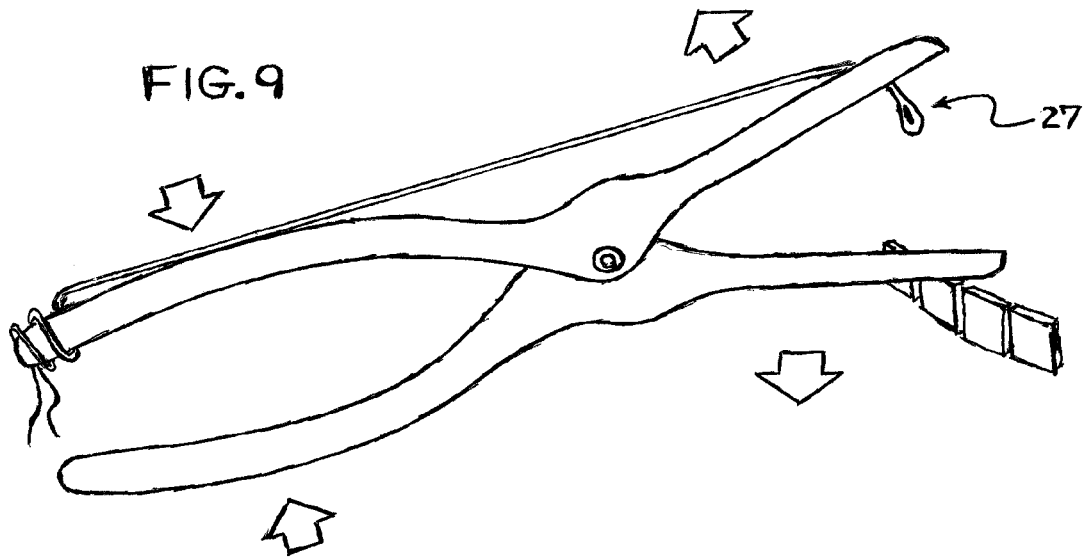

FIG. 9 shows the pliers having been squeezed and the debris 27 dislodged from between the teeth.

Figure 10:
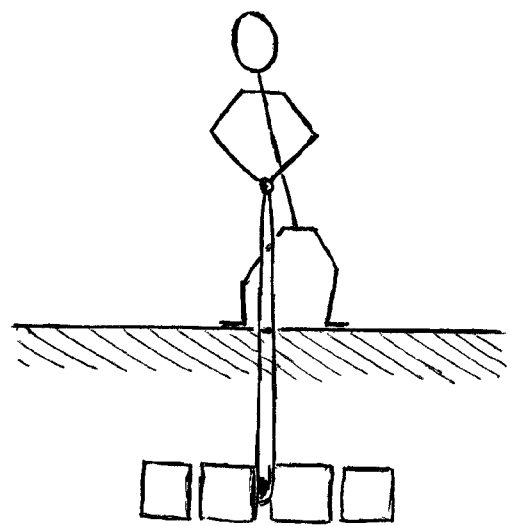
Figure 11:
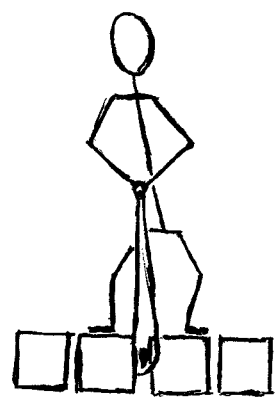

FIG. 10 and FIG. 11 illustrate the difference between the method and uniqueness of the present invention and other currently used methods. FIG. 10, which represents other methods, shows a stick person standing on a wall applying an upward force on the floss which in turn pulls up on the debris which in turn pulls up on the teeth as long as the debris stays lodged between the teeth. Because of the laws of physics, we know that for every force applied to a fixed point there is an equal and opposite force, which in this case the downward force is provided by the feet on the wall. Our concern therefore is, as we apply upward pressure (or force) on the debris, the same upward force is applied to the teeth risking the chance of loosening the teeth (or crown).

Figure 1:
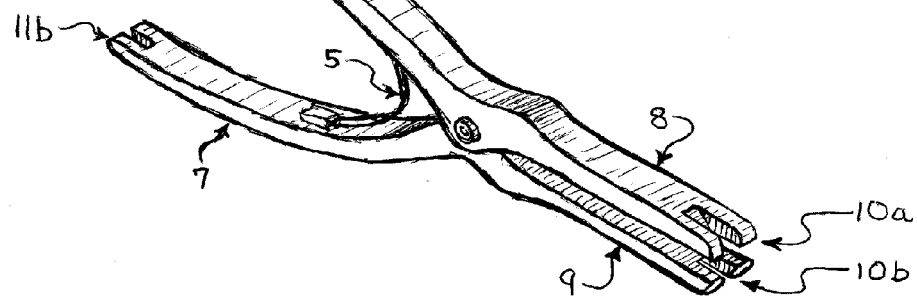
Figure 2:
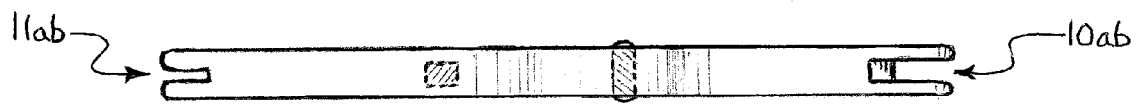

However, FIG. 11, which represents the present invention, shows the stick person pushing against the teeth themselves with the feet. As the person pulls up on the debris (accomplished by tip 8 in FIG. 1), it's upward force, which is transferred to the teeth, is canceled completely by the downward force on the teeth by the feet (accomplished by tip 9 in FIG. 1).

Because both upward and downward forces on the teeth are always equal, the resultant net force is always zero (0). Therefore, in this present invention, any force can be applied to the debris itself without loosening the teeth or crown.

The invention claimed is:

1. A dental tool comprising;
an elongated first element having proximal and distal ends; said first element comprises a first curved handle located at the distal end and a first tip located at the proximal end;
an elongated second element having proximal and distal ends; a second curved handle located at one end and a second tip located at an opposing end;
A first slot located in each said tip and a second slot located in each said distal end of the elongated member, the second slot being smaller than the first slot,
two strands of floss are fed through both first slots extending along one of the elongated elements and anchored to it's corresponding second slot;
the first element having a convex portion located between the first handle and first tip, the second element having a concave portion located between the second tip and the second handle; the convex portion and the concave portion pivotally secured together by a rivet such that the tips are located in an overlying relation; whereby when the handles are squeezed together the tips separate from one another.

2. A dental tool as claimed in claim 1 above, wherein the first and second tips are flat and flush with one another.

3. A dental tool as claimed in claim 1 above, wherein rubber pads are embedded on an outside surface of the first and second tips.

4. A dental tool as claimed in claim 1 above, further comprising a flat spring disposed between the handles so as to bias the handles apart and maintain the tips in a closed position.

* * * * *